United States Patent [19]

Obenaus et al.

[11] 4,000,199
[45] Dec. 28, 1976

[54] PROCESS FOR THE PRODUCTION OF ACETONE

[75] Inventors: Fritz Obenaus; Wilhelm Droste, both of Marl, Germany

[73] Assignee: Chemische Werke Huels Aktiengesellschaft, Marl, Germany

[22] Filed: Mar. 26, 1975

[21] Appl. No.: 562,360

[30] Foreign Application Priority Data

Mar. 29, 1974 Germany .......................... 2415151

[52] U.S. Cl. .......................................... 260/593 R
[51] Int. Cl.$^2$ ........................................ C07C 45/00
[58] Field of Search ................................ 260/593 R

[56] References Cited

UNITED STATES PATENTS

| | | | |
|---|---|---|---|
| 1,949,412 | 3/1934 | Dreyfus | 260/593 R |
| 3,384,668 | 11/1964 | Canter et al. | 260/593 R |
| 3,496,197 | 2/1970 | Van Rheenen | 260/593 R |
| 3,767,711 | 10/1973 | Gobron et al. | 260/593 R |
| 3,804,902 | 4/1974 | Sakakibara et al. | 260/593 R |

FOREIGN PATENTS OR APPLICATIONS 1,133,882  11/1968  United Kingdom ........... 260/593 R

OTHER PUBLICATIONS

Volta et al., J. of Catalysis, vol. 34, pp. 329–337 (1974).

*Primary Examiner*—James O. Thomas, Jr.
*Assistant Examiner*—James H. Reamer
*Attorney, Agent, or Firm*—Millen, Raptes & White

[57] ABSTRACT

Acetone is produced by the catalytic, oxidative decarbonylation of isobutyraldehyde in the gaseous phase by contacting a gaseous mixture of 1–15% by volume of isobutyraldehyde, at least a stoichiometric amount and up to about 30% by volume of oxygen, and an inert diluent, with a copper oxide catalyst.

14 Claims, No Drawings

PROCESS FOR THE PRODUCTION OF ACETONE

BACKGROUND OF THE INVENTION

This invention relates to a process for the production of acetone by the catalytic, oxidative decarbonylation of isobutyraldehyde.

Isobutyraldehyde, obtained in very large amounts as an unavoidable by-product during the manufacture of n-butyraldehyde from propylene by the oxo synthesis, has heretofore been utilized almost exclusively only in power plants for its calorific value.

Many experiments have been conducted to find a more economical use for isobutyraldehyde. Thus, it is known to split isobutyraldehyde into its starting components, propylene, carbon monoxide, and hydrogen (DAS [German Published Application] No. 1,917,244) and to react isobutyraldehyde to obtain synthesis gas. See German Unexamined Laid-Open Application DOS No. 1,767,281. However, the economic value of these products is only minor. Furthermore, attempts have been made to convert isobutyraldehyde into valuable products by oxidation. It is known to react isobutyraldehyde in the liquid phase with oxygen-containing gases in the presence of metallic oxide dispersions of molybdenum, chromium, silver, nickel, vanadium, tungsten, titanium, cerium, manganese, or cobalt as the catalyst and in the presence of a liquid diluent, such as isobutyric acid or the 2-ethylhexyl ester of 2-ethylhexanecarboxylic acid or silicone oil, to produce acetone, isopropanol, and isobutyric acid, German Application DAS No. 1,956,018. However, in this process, the yield and selectivity are relatively low. An improved selectivity is obtained in a process described in DOS No. 2,157,307 (U.S. Pat. No. 3,804,902). In this method, isobutyraldehyde is oxidized to acetone in the gaseous phase with oxygen on a catalyst of manganese oxide and optionally an alkali metal oxide on activated aluminum oxide as the support. With a 93% isobutyraldehyde conversion, the yield of acetone is 85 molar percent, based on the converted isobutyraldehyde and with a 98% isobutyraldehyde conversion, the acetone yield is only 83 molar percent.

For an economical production of acetone, as nearly complete as possible isobutyraldehyde conversion is required because the volatility of acetone is similar to that of the isobutyraldehyde, making separation difficult. Another difficulty arises from high portions of unconverted isobutyraldehyde by the unavoidable oxidation to isobutyraldehyde with excess oxygen during condensation. Therefore, the acetone yields attained according to the above-described process are unsatisfactory, especially at a high isobutyraldehyde conversion. Also, due to the complete combustion of approximately one-fifth of the isobutyraldehyde, the yield of acetone is proportionately reduced. Additionally, the removal of the additional heat from the reactors becomes a technical problem of reaction, because of the very high heat of reaction for the total combustion of the isobutyraldehyde.

It is well known that the load on the catalyst, i.e., the quantity of isobutyraldehyde fed per unit time, must be adapted to the discharge possibilities for the heat of reaction to avoid temperature profiles which are too steep, because high peak temperatures reduce the selectivity of the oxidation. A reduction in total heat of combustion permits a correspondingly higher load on the catalyst and thus a higher space-time yield of acetone. For conducting the process on a large technical scale, the space-time yield, i.e., the amount of product obtainable per catalyst volume and time, is always of great importance.

Consequently, it is an object of this invention to provide a process for the production of acetone by the catalytic, oxidative decarbonylation of isobutyraldehyde at an elevated temperature in the gaseous phase, which has a very high selectivity with respect to the formation of acetone even at a very high isobutyraldehyde conversion, and thus has simultaneously a lower total combustion of isobutyraldehyde. Other objects will be apparent to those skilled in the art.

SUMMARY OF THE INVENTION

According to this invention, a gaseous mixture of 1–15% by volume of isobutyraldehyde, at least the stoichiometric amount, but at most about 30% by volume of oxygen, and an inert gaseous diluent is passed over a catalyst of copper oxide at an elevated temperature with a contact time of 0.1 – 10 seconds.

DETAILED DISCUSSION

The copper in the freshly prepared catalysts employed in the process consists essentially of copper (II) oxide. The oxidation stage of the copper oxide during the oxidation process is not known.

The catalysts of this invention can be pure copper oxide or copper oxide on a suitable support. The copper oxide can be prepared in accordance with conventional methods, e.g. by thermal decomposition of copper salts as nitrates or nitrites, by oxidative degradation of organic copper salts as formiates, acetates, acetylacetonates, by oxidation of metallic copper as wire, chips or in pulverulant form and by precipitation of copper ions with alkali and subsequent dehydration. A pure copper oxide catalyst can be manufactured, for example, by precipitating a copper salt with an alkali as copper hydroxide, washing until the washing water shows an alkaline-free reaction, and subsequent dehydration of the copper hydroxide to copper oxide.

Suitable supports for the copper oxide are materials which have low inherent activity or better which are essentially inert under the reaction conditions and which also satisfy the usual requirements, for example, with respect to mechanical stability and structure. Certain commercial catalysts supports have proven to be advantageous, the main component of which is aluminum oxide or zinc oxide. When using other supports, in view of the widely varied ingredients thereof which can be present, for example, in the various commercial aluminum oxides, it is necessary to prove that the specific support per se has no or only low inherent activity under the elevated temperature of the reaction.

An advantageously simple method to produce the supported catalysts is the use of aqueous solutions of water-soluble copper salts, e.g., $Cu(CH_3COO)_2 \cdot H_2O$, for impregnating the support. The copper salt on the dried, impregnated support can then be converted into copper oxide in a conventional manner by heating in the presence of oxygen. Of course, it is also possible to employ other known methods, such as, for example, the precipitation of copper oxide onto a solid support, for coating the supports with the copper oxide. In the case of supported catalysts, only those are employed whose support surface has a layer of the copper oxide catalyst.

The copper oxide content of the catalyst is not critical. However, care should be taken that the support surface is completely coated with copper oxide to reduce a possible detrimental influence of the support under the reaction conditions. In general, a copper oxide proportion of from about 1% by weight (based on the finished catalyst) is sufficient for the coating process, while a copper oxide layer of more than 10% by weight does not have any advantages. Consequently, catalysts are preferably employed which have a copper oxide content of 1–10% by weight. Supported catalysts are preferred since they exhibit improved mechanical stability compared to the pure copper oxide catalysts and can be produced more economically.

An additional impregnation of the catalyst with dissolved alkali metal hydroxides can lead to a further increase in the acetone yield when a supported catalyst is utilized. A layer with about 0.1% by weight of an alkali metal hydroxide (based on the finished catalyst) is suitable, but the optimum dose depends, in a manner not completely explained, on the type and characteristics of the support utilized and on the quantity of the applied copper oxide. A coating with more than 0.5% by weight of alkali metal hydroxide did not prove advantageous, since then a reduction in activity and selectivity is observed. With a coating of less than 0.05% by weight, the effect of the doping hydroxide drops increasingly. The impregnation, preferably with aqueous alkali metal hydroxide solution, can be accomplished before as well as after the impregnation with the aqueous copper salt solution. Unless a preformed catalyst support is used, the catalyst must furthermore be brought into a suitable shape. This is done in the conventional manner, for example, by combining the catalyst with an auxiliary tabletting agent, e.g., graphite, stearic acid, polyethylene, or mixtures thereof, and then tabletting the mixture. The catalyst can be in any convenient form, e.g., in spherical, tablet, bar, pill, or piece form.

The oxidation temperature, although elevated, should be maintained at as low a value as possible to avoid further oxidation of the already formed acetone. In general, interior reactor temperatures of 150°–300° C. are suitable. Although a pronounced reaction still occurs even below this temperature range, the reaction rate below 150° C. is generally too low for a technical process. Above 300° C., the yield of acetone, based on the isobutyraldehyde employed, is markedly lower. Especially good results are achieved in the range of 180°–280° C.

Economically feasible contact times normally range from 0.1 to 10 seconds, preferably 0.5 – 5 seconds, calculated on the total amount of feed gas under the reaction conditions and based on the catalyst bulk factor. Accordingly, contact time means the time period required by a segment of the gaseous mixture under the reaction conditions to travel through the space occupied by the bulk of the catalyst.

The reaction is ordinarily conducted under normal pressure or under only slightly elevated pressure. However, it is also possible basically to conduct the reaction under vacuum or under superatmospheric pressure. In this connection, it is merely necessary to provide the conditions for maintaining a gaseous phase.

The two carbon oxides, viz., CO and $CO_2$, occur as byproducts during the reaction. In general, the proportion of CO amounts to a multiple of the $CO_2$ proportion, so that the waste gas can be used, after freed of acetone, additionally advantageously as heating gas or, after furthermore removing the $CO_2$, also as a CO source for syntheses.

Oxygen in a mixture with an inert diluent is used as the oxidizing agent. The oxygen should be employed in at least a stoichiometric amount, i.e., 1 mole of oxygen per mole of isobutyraldehyde, since complete isobutyraldehyde conversion is impossible with smaller amounts of oxygen. It is advantageous to use oxygen in a molar excess with respect to the isobutyraldehyde so that the reaction gas, after passing through the catalyst bed, still contains oxygen even with a complete conversion of the isobutyraldehyde. A more uniform temperature profile is thereby established over the length of the catalyst bed and corresponding more uniform exploitation of the entire catalyst, thus permitting higher space-time yields. Normally, air is used as the oxidation agent. Only in case of high isobutyraldehyde contents in the feed gas is a slight enrichment of the air with oxygen sometimes necessary to complete the conversion. However, the feed gas should not contain more than 30% by volume of oxygen, advantageously. Larger oxygen contents do not offer any advantages and result in higher expenses due to the addition of the expensive oxygen. In case the feed gas contains small quantities of isobutyraldehyde, a high excess of oxygen is quite possible, up to a molar ratio of IBA : $O_2$ = 1 : 10, as can occur, for example, with the use of air. In case of a high content of isobutyraldehyde in the feed gas starting with about 10% by volume, the oxygen excess will suitably be kept at a lower level and will approach to an increasing extent the stoichiometric ratios, since a higher oxygen content merely causes additional expenses.

The isobutyraldehyde content in the feed gas suitably is 1–15% by volume. With isobutyraldehyde contents below 1% by volume, the process no longer is economical due to increased costs of separation of the thus-produced acetone. With isobutyraldehyde contents in the starting gas of above 15% by volume, the desired, complete conversion can no longer be attained economically on the technical scale, due to the high heat of reaction. Suitably, feed mixtures with isobutyraldehyde contents of 2–10% by volume are employed. Especially suitable as the inert diluent of the gaseous mixture is nitrogen and/or steam, but it is also possible to utilize the carbon oxides contained in the reaction waste gas as diluting agents. The use of nitrogen is advantageous, since air is the cheapest and thus the preferred oxidizing agent. The addition of steam improves the removal of the heat produced during the reaction, thus attaining a higher space-time yield and a better selectivity of the reaction. Also, steam, compared to non-condensable diluents, facilitates the acetone separation from the reaction gases, since the parts by volume of the non-condensable gases are correspondingly reduced. Normally, steam is used in amounts of up to 70% by volume, based on the entire starting gas mixture, but it is also possible to use even larger amounts of steam, although not economically. Advantageously, it is also possible to employ mixtures of several inert diluents, for example, mixtures of air and steam. Also, the gases leaving the reactor can be recycled into the latter, after the thus-formed acetone has been separated, and can be used as diluents.

Although explosive gaseous mixtures can be used as feed gases in the process of this invention, if suitable safety measures are taken, it is preferred to utilize gaseous mixtures not capable of explosion when conducting the reaction on a large technical scale.

The advantages attainable with the process of this invention are, above all, that isobutyraldehyde is very selectively converted to acetone at high conversions and, due to the high selectivity, only a minor portion of the isobutyraldehyde is completely combusted, so that consequently less heat of reaction needs to be removed, whereby a high space-time yield is achieved.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Under agitation, a solution of 75 g. of NaOH in 1.5 liter of distilled water is added at room temperature to a solution of 150 g. of $Cu(NO_3)_2 \times 3\ H_2O$ in 4 l. of distilled water. Thereafter, the solution is vacuum-filtered and the thus-precipitated $Cu(OH)_2$ is washed free of alkali with distilled water. By heating for 15 hours to 150° C., the $Cu(OH)_2$ is converted to CuO and dried. The CuO is finely pulverized and combined with 0.5% by weight of graphite and then thoroughly mixed. The resulting powder is then compressed into pills (diameter, 6 mm.; thickness, 2 mm.). The CuO pills are subsequently finished by heating for 3.5 hours at 400° C. under air. The reaction is conducted in a quartz glass reactor thermostated with the aid of a salt bath. The reactor consists of a quartz glass tube having an inside diameter of 22 mm. with a concentrically running thermocouple sleeve with a diameter of 6 mm. The catalyst, disposed on a porous quartz support, fills, with a bed length of 71 mm., an annular space of 25 cm³. The starting material used is a gaseous mixture containing 3% by volume of isobutyraldehyde (IBA), 74% by volume of air, and 23% by volume of water. With a contact time of 2.7 seconds and an internal reactor temperature having a temperature maximum of 245° C., the isobutyraldehyde conversion is 92.2% and the acetone yield, based on converted isobutyraldehyde (IBA) amounts to 92 molar percent.

If the water in the starting gaseous mixture is replaced by nitrogen, an IBA conversion of 91.5% is obtained under identical reaction conditions, and an acetone yield is obtained which is 90 molar percent, based on converted isobutyraldehyde (IBA). Under both reaction conditions, the two carbon oxides CO and $CO_2$ are found as by-products in the waste gas in a molar ratio of about 2 : 1.

EXAMPLE 2

Under heating, 14 g. of copper (II) acetate $\times\ H_2O$ is dissolved in 85 ml. of water. Then, 125 g. of $Al_2O_3$ (commercial catalyst support, Type H 0416, manufacturer: Catalyst Plant Houdry-Huels, rods 1.6 mm. diameter × 5 mm., calcined at 600° C.), are impregnated with the aqueous copper acetate solution. The water is thereafter removed in a forced-circulation evaporator under vacuum at a bath temperature of 50° C. The thus-impregnated catalyst is now dried for 16 hours at 110° C. and calcined for 4 hours at 350° C. in the presence of air. As the starting material, a gaseous mixture is employed containing 4% by volume of IBA, 43.5% by volume of air, and 52.5% by volume of $N_2$. With a contact time of 2.6 seconds and an internal reactor temperature having a temperature maximum of 270° C., the isobutyraldehyde conversion is 98.4%; the yield of acetone, based on converted isobutyraldehyde, is 84 molar percent.

If the proportion of nitrogen in the feed gas mixture is partially replaced by water, an IBA conversion of 99.2% is achieved with a starting gaseous mixture with 4% by volume of IBA, 43.5% by volume of air, 10.5% by volume of $N_2$, 42% by volume of $H_2O$, with a contact time of 2.6 seconds and an internal reactor temperature of maximally 270° C. The yield of acetone, based on converted isobutyraldehyde, is 88 molar percent.

EXAMPLE 3

In accordance with the procedure described in Example 2, the $Al_2O_3$ support of Example 2 is impregnated with Cu(II) acetate $\times\ H_2O$. After the water has been removed, 130 g. portions of the catalyst are impregnated with a solution of 0.1 g. and 0.5 g. of NaOH, respectively, in 80 ml. of water. The excess water is removed under vacuum by means of a forced-circulation evaporator at a bath temperature of 50° C. The thus-impregnated catalysts, which are dried for 16 hours at 110° C. and calcined for 4 hours at 350° C. in the presence of air, each contain 4.27% by weight of CuO and contain 0.08% by weight and 0.38% by weight, respectively, of NaOH. With a feed gas mixture of 4% by volume of IBA, 43.5% by volume of air, 10.5% by volume of $N_2$, 42% by volume of $H_2O$, and with a contact time of 2.6 seconds, the following conversions and yields are obtained with an internal reactor temperature maximum of 270° C.:

| Catalyst | IBA Conversion | Acetone Yield Based on Converted IBA, in mol-% |
|---|---|---|
| 4.27% by wt. CuO on $Al_2O_3$ (Example 2) | 99.2 | 88 |
| 4.27% by wt. CuO + 0.08% by wt. NaOH on $Al_2O_3$ | 99.4 | 93 |
| 4.27% by wt. CuO + 0.38% by wt. NaOH on $Al_2O_3$ | 99.0 | 85 |

If the catalysts are impregnated during their manufacture with KOH or LiOH instead of NaOH, practically identical values are obtained for the IBA conversions and the conversion yields of acetone, under the same reaction conditions.

EXAMPLE 4

According to the procedure described in Example 3, a catalyst is produced with 4.27% by weight of CuO and 0.08% by weight of NaOH on $Al_2O_3$ (Type: H 0415, Catalyst Plant Houdry-Huels, bars 2.4 mm. diameter × 5 mm., calcined at 600° C.). With a feed mixture of 4% by volume of IBA, 43.5% by volume of air, 10.5% by volume of $N_2$, and 42% by volume of $H_2O$, an IBA conversion of 98% is attained with a contact time of 2.6 seconds and with an internal reactor temperature of maximally 270° C. The yield of acetone, based on converted IBA, amounts to 85 molar percent.

EXAMPLE 5

According to the procedure described in Example 3, a catalyst is prepared with 4.27% by weight of CuO and 0.08% by weight of NaOH on $Al_2O_3$ (E. Merck, product No. 1095, grain size 0.03 – 0.25 mm.). After the impregnation, the catalyst is dried in air at 110° C. for 18 hours. Thereafter, the catalyst is combined with 10% stearic acid, well intermixed, and compressed into pills (height 3 mm., diameter 4 mm.). The pills are finished by heating in air for 7 hours at 200° C. and for 4 hours at 350° C. The reaction is conducted under the same conditions as in Example 3. The IBA conversion is 99.1%, the acetone yield, based on reacted IBA, is 93 molar percent.

EXAMPLE 6

According to the procedure of Example 2, a catalyst is produced with 4.27% by weight of Cu on a zinc oxide support (catalyst support type: H 2004, Catalyst Plant Houdry-Huels, rods 6 mm. diameter × 3 mm.). The zinc oxide used as the support contains, in addition to ZnO, smaller proportions of $Al_2O_3$, CaO, $K_2O$, and $Cr_2O_3$ and showed the least inherent activity of all supports. On this impregnated catalyst, with a mixture of starting material consisting of 71% by volume of air, 3% by volume of IBA, and 26% by volume of $H_2O$ and with a contact time of 3.7 seconds with a conversion of 90.5% IBA, an acetone yield was obtained of 96 molar percent, based on the IBA converted. The maximum internal reactor temperature was 225° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of acetone by the catalytic, oxidative decarbonylation of isobutyraldehyde in the gaseous phase wherein a gaseous mixture of 1–15% by volume of isobutyraldehyde, at least a stoichiometric amount and up to about 30% by volume of oxygen, and an inert diluent, is contacted with a metal oxide catalyst, the improvement wherein the metal oxide is copper oxide.

2. A process according to claim 1, wherein the gaseous mixture is contacted with the catalyst for a time of 0.1 – 10 seconds.

3. A process according to claim 1, wherein the catalyst is a supported catalyst having a copper oxide content of 1–10% by weight, based on the finished catalyst.

4. A process according to claim 4, wherein the catalyst contains about 0.05 – 0.5% by weight of an alkali metal hydroxide, based on the finished catalyst.

5. A process according to claim 1, wherein the gaseous mixture contains 2–10% by volume of isobutyraldehyde.

6. A process according to claim 1, wherein the process is conducted at a temperature of 150°–300° C.

7. A process according to claim 1, wherein the process is conducted at a temperature of 180°–280° C.

8. A process according to claim 1, wherein the inert diluent comprises nitrogen.

9. A process according to claim 8, wherein the gaseous mixture comprises isobutyraldehyde and air.

10. A process according to claim 1, wherein the inert diluent comprises steam.

11. A process according to claim 1, wherein the gaseous mixture is a mixture of air, isobutyraldehyde and steam.

12. A process according to claim 11, wherein a stream of the gaseous mixture containing 2–10% by volume of isobutyraldehyde is passed at 180°–280° C. with a contact time of 0.5 to 5 seconds through a bed of a copper oxide coated supported catalyst having a copper oxide content of 1–10% by weight, based on the finished catalyst, and about 0.05 – 0.5% by weight of an alkali metal hydroxide, based on the finished catalyst.

13. A process according to claim 12, wherein the support has as its main component aluminum oxide or zinc oxide.

14. A process according to claim 12 wherein the gaseous mixture contains nitrogen in excess of that present in the air and an excess of stoichiometric amount of oxygen.

* * * * *